United States Patent
Chatterjee et al.

(10) Patent No.: US 7,611,734 B2
(45) Date of Patent: Nov. 3, 2009

(54) **USE OF EXTRACTS FROM *PELARGONIUM* SPECIES**

(75) Inventors: Shyam Sunder Chatterjee, Karlsruhe (DE); Egon Koch, Karlsruhe (DE); Michael Nöldner, Karlsruhe (DE)

(73) Assignee: ISO Arzneiminel GmbH & Co. KG, Ettlingen (DE)

( * ) Notice: Subject to any disclaimer, the term of this patent is extended or adjusted under 35 U.S.C. 154(b) by 0 days.

(21) Appl. No.: 10/571,119

(22) PCT Filed: Oct. 26, 2004

(86) PCT No.: PCT/EP2004/012069

§ 371 (c)(1),
(2), (4) Date: Mar. 8, 2006

(87) PCT Pub. No.: WO2005/041993

PCT Pub. Date: May 12, 2005

(65) Prior Publication Data

US 2007/0014877 A1    Jan. 18, 2007

(30) Foreign Application Priority Data

Oct. 29, 2003    (DE) ............................... 103 50 338

(51) Int. Cl.
*A01N 65/00*    (2006.01)
*A01N 25/00*    (2006.01)
(52) U.S. Cl. ...................... 424/725; 514/783
(58) Field of Classification Search ............ None
See application file for complete search history.

(56) References Cited

U.S. PATENT DOCUMENTS

2002/0187115 A1    12/2002    Pushpangadan et al.

FOREIGN PATENT DOCUMENTS

| GB | 2 355 189 A | 4/2001 |
| GB | 2 381 195 A | 4/2003 |
| WO | WO-96/05849 | 2/1996 |
| WO | WO-03/028746 A1 | 4/2003 |
| WO | WO03028746 * | 4/2003 |

OTHER PUBLICATIONS

Kolodziej, Traditionally used *Pelargonium* species: chemistry and biological activity of umckaloabo extracts and their constituents. Current Topics in Phytochemistry 3: 77-93, 2000.*
Kayser et al., Antibacterial activity of extracts and constituents of *Pelargonium sidoides* and *Polargonium reniforme*. Planta Medica 63: 508-510, 1997.*
Greenway et al., Research: Relief of Post-Herpetic Neuralgia Pain with Topical Geranium Oil [Fibromyalgia & Pain related news]. Fibromyalgiasupport.com, Oct. 10, 2003.*
Bourin et al, European Journal of Pharmacology 463: 55-65, 2003.*
Hascoet et al, Prog. Neuro-Psychuat 25: 141-166, 2001.*
Phillipson, Phytotherapy Research 13: 2-8, 1999.*
Revilla et al, J. Agric. Food Chem 46: 4592-4597, 1998.*
Haidvogl et al., Acute bronchitis in children, Zeitschrift fur Phytotherapie, (1996) vol. 17, No. 5, pp. 300-313.*
Sampair et al., Immune activation by *Corynebacterium parvum* antigen induces alterations of circadian rhythm in C57B/6 mice, Society for Neuroscience Abstracts, (2001) vol. 27, No. 2, pp. 2236. print.*
Kayser et al., Immunomodulatory principles of *Pelargonium sidoides*, Phytotherapy research : PTR, (Mar. 2001) vol. 15, No. 2, pp. 122-126.*
Haidvogl et al. Zeitschrift fur Phytotherapie, 17(5):300-313 (1996); XP008011447.
Kolodziej et al., Zeitschrift fur Phytotherapie, 19(3):141-151 (1998); XP008011448.
Yirmiya, Current Opinion on Psychiatry, 10:470-476 (1997).
Dantzer, Brain, Behavior, and Immunity, 18:1-6 (2004).
Miller, Brain, Behavior, and Immunity, 17:S132-S134 (2003).
Reichenberg et al., Arch. Gen. Psychiatry, 58:445-452 (2001).
Kent et al., TiPS, 13:24-28 (1992).
Kozak et al., The American Physiological Society, pp. R1298-R1307 (1997).
Dantzer, Brain, Behavior, and Immunity, 15:7-24 (2001).
Kelley et al., Brain. Behavior, and Immunity 17:S112-S118 (2003).
Dantzer et al., Brain, Behavior, and Immunity, 17:S119-S124 (2003).
Pall, Medical Hypotheses (57(2):139-145 (2001).
Miller et al., Health Psychology, 21(6):531-541 (2002).

(Continued)

*Primary Examiner*—Michele Flood
*Assistant Examiner*—Qiuwen Mi
(74) *Attorney, Agent, or Firm*—Peter F. Corless; Christine C. O'Day; Edwards Angell Palmer & Dodge LLP

(57) ABSTRACT

The use of extracts from *Pelargonium* species or plant parts thereof, particularly from *P. sidoides* and *P. reniforme* for the prophylaxis or treatment of disease-related behavioral changes, the chronic or post-viral asthenia syndrome and/or stress-induced chronic pathological conditions as well as pharmaceutical preparations containing these extracts are described.

2 Claims, No Drawings

OTHER PUBLICATIONS

Kolodziej et al., Phytomedicine, 10(Suppl. IV):18-24 (2003).

H. Matthys et al., "Efficacy and safety of an extract of *Pelargonium sidoides* (EPs 7630) in adults with acute bronchitis—A randomised, double-blind, placebo-controlled trial", *Phytomedicine*, vol. 10, Supplement 4, pp. 7-17 (2003).

M. Haidvogl et al., "Treatment effect and safety of EPs 7630-solution in acute bronchitis in childhood: Report of a multicentre observational study", *Phytomedicine*, vol. 14, Supplement 6, pp. 60-64 (2007).

M. Bourin et al., "The mouse light/dark box test", *European Journal of Pharmacology*, vol. 463, pp. 55-65 (2003).

P.W. Laidler et al., "The Magic Medicine of the Hottentots", *South African Journal of Science*, vol. XXV, pp. 433-447 (1928).

M. Heger et al., "Non-streptococcal tonsillo-pharyngitis in children: Efficacy of an extract from *Pelargonium sidoides* (EPs 7630) compared to placebo", *Phytopharmaka VII*, (2002).

H. Kolodziej et al., "Medicinal Use of South African Pelargoniums—Studies of *Perlargonium sidoides* and *P. reniforme*", *Deutsche Apotheker Zeitung*,, 135(10), pp. 23-34 (1995).

I. Konig et al., "Respiratory Tract Therapy on a Natural Basis", *Therapie Woche*, vol. 45, pp. 1123-1126 (1995).

A. Sechehaye et al., "The treatment of organic and surgical tuberculosis with Umckaloabo—Internal healing methods (Stevens cure)—Historical aspects, experimental research, clinical observations, results", *English translation of the last chapter of (VI: Conclusions)*, pp. 140-141 (1937).

B. Blochin et al., "Umckaloabo compared with acetylcysteine in children with acute bronchitis—A prospective, randomized, controlled opens tudy of efficacy and tolerability", *Translation from Der Kassenarzt*, pp. 46-50 (1999).

M. Hascoet et al., "The mouse light-dark paradigm: A review", *Prog. Neuro-Phychopharmacol. & Biol. Phychiat*, vol. 25, pp. 141-166 (2001).

Mnyamezeli Nxakala's Affidavit (2008).
Elizabeth Nkqayi's Affidavit (2008).
Zamile Ngethu's Affidavit (2008).
Yaziew Gidi's Affidavit (2008).
Notsomi Bevile's Affidavit (2008).
Notini Cylvia Khulungu's Affidavit (2008).

Red List 2002—Medicinal Product Register for Germany (including medicinal products approved in the EU and certain medical devices); Editor: Rote Liste® Service GmbH, Frankfurt/Main; ECV—Editio Cantor Verlag, Aulendorf.

Red List 2003—Medicinal Product Register for Germany (including medicinal products approved in the EU and certain medical devices); Editor: Rote Liste® Service GmbH, Frankfurt/Main; Editio Cantor Verlag, Aulendorf.

Information for Patent/Patent Application: "Umckaloabo® Solution"; Approval No. 57602 (Swissmedic); Approval Holder: Schwabe Pharma AG, Kussnacht am Rigi.

Internet address: www.gesundheit.de, "Common Cold, Influenza, Influenza Infection" (2005).

Internet address: www.medizininfo.de/immunsystem/erkaelt/erkaeltung.htm, "Immune System", (2008).

H. Lewitzka-Reitner et al., "Grosses Gesundheits-Lexikon—An Encyclopedia concerning health related topics" (1987).

"Rigorous limitation for indication of UMCKALOABO", *Arznel-telegramm 2006*, 37(10), pp. 92-93 (2006).

"Benefit of *Pelargonium* extract (UMCKALOABO) in accute bronchitis documented", *Arznei-Telegramm*, 39(10), pp. 104-106 (2008).

M. Viljoen et al., "Non-termination of sickness behavior as precipitating factor for mental disorders", *Medical Hypotheses*, vol. 65, pp. 316-329 (2005).

M.L. Pall et al., "Common epiology of posttraumatic stress disorder, fibromyalgia, chronic fatigue syndrome and multiple chemical sensitivity via elevated nitric oxide/peroxynitrite", *Medical Hypotheses*, 57(2), pp. 139-145 (2001).

R. Yirmiya et al., "Behavioral and psychological effects of immune activation: implications for 'depression due to a general medical condition'", *Current Opinion in Psychiatry*, vol. 10, pp. 470-476 (1997).

S. Kent et al., "Sickness behavior as a new target for drug development", *TiPS*, vol. 13, pp. 24-28 (1992).

* cited by examiner

USE OF EXTRACTS FROM *PELARGONIUM* SPECIES

The present invention relates to the use of extracts from *Pelargonium* species or plant parts thereof, particularly from *P. sidoides* and *P. reniforme* for the prophylaxis or treatment of disease-related behavioural changes, chronic or post-viral asthenia syndrome and/or stress-induced chronic pathological conditions, as well as pharmaceutical preparations containing these extracts.

Many patients know from their personal experience that infections and inflammations such as a cold, influenzal infections or infections of the upper respiratory tracts are accompanied by a plurality of unspecific and generalized disease symptoms. Besides phenomena such as fever and articular or muscular pain, also behavioural changes are among them. Thus, episodes of depression, listlessness, feeling of weakness, fatigue, anergy, anorexia, social isolation, weakness of concentration, sleep disorders, anxiety, indifferentism or hyperalgesia often occur in connection with infective diseases. In their totality, these symptoms and behavioural disorders are designated as "acute phase reaction", "sickness behaviour" or "depression due to a generalized disease" (W. Kozak et al., Am. J. Physiol. 272, R1298-R1307 (1997); R. Dantzer, Brain Behav. Immun. 15, 7-24 (2001); K. W. Kelley et al., Brain Behav. Immun. 17, p. 112-p. 118 (2003); A. H. Miller, Brain Behav. Immun. 17, p. 132-p. 134 (2003)).

On a molecular level these symptoms are caused by an increased synthesis of proinflammatory cytokines such as interleukuin-1 (IL-1), IL-6, tumor necrosis factor-$\alpha$ (TNF$\alpha$) or interferons (INF). These mediators, which are produced in increased amounts after tissue damages, elicit behavioural changes indirectly via afferent nerve tracts or directly after transfer into the brain. Although sickness behaviour clearly appears mainly in cases of infectious diseases, it is also observed in connection with injuries, traumata, tumor diseases or inflammatory reactions such as autoimmune diseases (R. Dantzer, Brain Behav. Immun. 15, 7-24 (2001)).

The importance of cytokines for the development of unspecific disease symptoms and behavioural changes was recognized for the first time in the scope of clinical studies. It turned out that the administration of, for example, IL-2 or interferons to patients with tumor diseases, hepatitis or multiple sclerosis causes influenza-like symptoms and psychiatric disorders (such as acute psychoses and serious depressions). Meanwhile, there is a plurality of indication that the cytokine-dependent mechanisms that contribute to disease-related behavioural changes play an important role also in the pathogenesis of depressions (L. Capuron and R. Dantzer, Brain Behav. Immun. 17, p. 119-p. 124 (2003)).

In test animals sickness behaviour can be caused by direct injection of proinflammatory cytokines or by administration of a cytokine inducer such as a lipopolysaccharide, which are constituents of the cell walls of gram-negative bacteria. Like in human beings, typical symptoms in animals are, inter alia, a reduced uptake of food and water, loss of weight, reduced social interactions, decreasing sexual behaviour, limited kinesic and exploratory behaviour or also a lack of interest for sweetened drinks.

The pathophysiologic importance of sickness behaviour presumably lies in an adaption of the organism to the modified needs of a diseased organism. As a result, exhausting physical activities (such as foraging and sexual behaviour) are avoided and temperature losses are limited (for example by physical rest). Simultaneously, the temperature production is increased, for example by trepidation. These behavioural changes in total shall ease the healing process for the body. However, this condition should only last until it is no longer necessary for the healing process. A number of mechanisms is known actually, which limit the biological effects of the proinflammatory cytokines such as the increased synthesis of gluco-corticoids, IL-10 or $\alpha$-melanocyte-stimulating hormone (R. Yirmiya, Current Opinion in Psychiatry 10, 470-476 (1997)). Perturbations of these regulative mechanisms may contribute to a continuation of the immunologic and neuronal processes and may lead to a misdirected adaption reaction which manifests as chronic weakness syndrome (burnout syndrome, chronic fatigue syndrome, chronic exhaustion syndrome) or as post-viral weakness syndrome (post-viral fatigue syndrome). Various stress-induced chronic disease conditions such as the posttraumatic stress, syndrome, fibromyalgia or multiple chemical sensitivity syndrome (multiple chemical sensitivity, sick building syndrome, electrical allergy), exhibit very similar symptoms and many patients fulfill the diagnostic criteria for one or more of these diseases. It is common to all of them that they are elicited by a state of stress which is followed by a longer lasting pathological condition. The preliminary stress is obviously the elicitor for the cell-promoting "circulus vitiosus". It becomes more and more evident that there are close relations between the nervous system, the immune system and the hormone system and that all these conditions are caused by a stress-induced reduced responsiveness of the immune system against anti-inflammatory signals (M. L. Pall (2001), Med. Hypotheses 57, 139-145; G. E. Miller et al. (2002), Health Psychol. 21, 531-541).

Due to their frequent and regular appearance, the symptoms of the sickness behaviour are often ignored by physicians. They are rather considered to be unpleasant side effects of the actual disease process, which cannot be avoided. However, it is clear from the knowledge obtained in recent years that the disease-related behavioural changes and the physiological reactions associated therewith (e.g. fever) are a complex pathological condition in themselves.

The symptoms of sickness behaviour can elicit a severe psychological strain in affected patients and impair the quality of life dramatically. In particular, the lethargic attitude associated therewith can significantly hamper the patient's cooperation in therapeutic measures, such as in case of tumor diseases, or challenge the overall success of the treatment. Furthermore, in cases of trivial diseases such as an influenzal infection, the degree of severity of the symptoms of the disease-related behavioural changes is often not in due proportion to the, actual physiological purpose of this defensive mechanism.

The elucidation of the molecular mechanisms of sickness behaviour has led to new possible ways for a therapeutic intervention in recent years. Antidepressive agents have turned out to be suitable for the treatment of the depressive component of disease-related behavioural changes. However, antidepressive agents develop their therapeutic effect after a delay of several days or weeks and additionally often induce severe side effects. Therefore, for acute or less severe diseases these medicaments are not suitable or are of limited suitability only. Furthermore, antidepressive agents do not exert any influence on the neurovegetative symptoms of sickness behaviour such as physical Weakness, exhaustion or anorexia. Therefore, there is an urgent need for effective treatment methods against disease-related behavioural changes that exhibit limited side effects.

Extracts from the roots of the *Pelargonium* species *P. sidoides* and *P. reniforme*, which are domiciled in South Africa, are widely used in the African traditional medicine for the treatment of diarrhea, gastrointestinal complaints, dysmenorrhoea and liver diseases. However, the administration against respiratory tract diseases and, particularly, against tuberculosis of the lung is predominant. Since many years, also an extract from the roots of *P. sidoides* is distributed under the trade name Umckaloabo for the treatment of acute and chronic infections of the otorhinolaryngologic regions such as rhinopharyngitis, tonsillitis, sinusitis and bronchitis. The clinical efficacy of this extract appears to rely on antimicrobial and immuno-modulating effects. There are evidences from experimental investigations that an extract from *Pelargonium sidoides* increases the synthesis of TNF-α, INF-β and nitric oxide. (NO) (H. Kolodziej et al., Phytomedicine 10 (Suppl. 4), 18-24 (2003)).

It now has been surprisingly observed that extracts from *Pelargoniums* positively influence LPS-induced behavioural changes in animal experiments despite the stimulating effect on the synthesis of proinflammatory cytokines and, thus, can be employed for the prophylaxis and therapy of disease-related behavioural changes ("sickness behaviour") in human beings and animals. Examples for the disease-related behavioural changes are symptoms such as episodes of depression, listlessness, feeling of weakness, fatigue, anergy, anorexia, social isolation, weakness of concentration, sleep disorders, anxiety, indifferentism or hyperalgesia, which occur in a temporal correlation with infectious diseases, injuries, traumata, tumor diseases, inflammatory reactions or autoimmune diseases. Furthermore, the extracts are suitable for the prophylaxis and treatment of sickness behaviour in connection with the therapeutic application of natural or recombinant cytokines such as interleukins, interferons and the like or also with the application of cytostatic agents or other cell or tissue-damaging medicaments or therapeutic measures. Moreover, *Pelargonium* extracts can also be used for the prophylaxis and therapy of the chronic or post-viral asthenia syndrome (chronic or post-viral fatigue syndrome) and various stress-induced chronic pathological conditions such as the posttraumatic stress syndrome, fibromyalgia or multiple chemical sensitivity.

Extracts from *Pelargoniums* or plant parts thereof can be obtained according to known production methods in various compositions using solvents such as water, methanol, ethanol, acetone and the like as well as mixtures thereof at temperatures from room temperature to 60° C. under slight to vigorous mixing or by percolation within 10 minutes to 24 hours. Preferred extraction solvents for this purpose are mixtures of ethanol and water, particularly preferred in a ratio ethanol/water=10/90 to 12/88 (w/w). In order to concentrate the active ingredients, further concentration steps can be carried out, such as liquid-liquid distribution using, for example, 1-butanol/water or ethylacetate/water, adsorption-desorption using ion exchangers, LH20, HP20. and other resins or chromatographic separations using RP18, silica gel and the like. If desired, further processing to obtain dry extracts is carried out according to methods known per se by removing the solvent at an increased temperature and/or reduced pressure or by freeze-drying.

The extracts according to the invention can be administered, preferably orally, in form of powders, granules, tablets, dragées (coated tablets) or capsules or as a solution such as that directly obtained by the extraction.

For the preparation of tablets, the extract is mixed with suitable pharmaceutically acceptable adjuvants such as lactose, cellulose, silicon dioxide, croscarmellose and magnesium stearate and pressed into tablets which are optionally provided with a suitable coating made of, for example, hydroxymethylpropyl cellulose, polyethylene glycol, colorants (e.g. titanium dioxide, iron oxide) and talcum.

The extracts according to the invention can also be filled into capsules, optionally after adding adjuvants such as stabilizers, fillers and the like. The dosage is such that 2 to 1000 mg, preferably 10 to 200 mg extract are administered per day.

The efficacy of *Pelargonium* extracts against disease-related behavioural changes and/or chronic or post-viral asthenia syndrome are supported by the experiments described below.

A dry extract from roots of *P. sidoides*, which was produced by means of a double maceration using seven times their amount made up of 11 percent by weight ethanol at 55° C., respectively, (yield: 11%), was used for the experiments. The extract was administered to male NMRI mice (20-25 g weight) by gavage in varying dosages in 0.2% agar suspension (10 ml/kg). Control animals received the agar suspension only. One hour after the treatment, the animals were injected intraperitoneally with 400 µg/kg lipopolysaccharide (LPS) (*E. coli* 0127:B8; Sigma, Deisenhofen) in 10 mg/kg physiological saline (0.9% NaCl). After a further two hours, the animals were transferred into the bright field of a dark-bright box and the motility as well as the exploration behaviour were observed over a period of 3 minutes. As nocturnal animals, mice prefer to stay in a dark surrounding. Therefore, an extended stay in the bright region of the bright-dark box and a decreasing frequency of changes between the two regions is to be assessed as an evidence for a reduced exploration behaviour, anergy and reduced interest. The results of the experiments are shown in the following table. It becomes evident that animals treated with LPS stay significantly longer in the bright region compared to control animals (NaCl) and change less often between the two regions. This effect is neutralized by the pre-treatment with the *Pelargonium* extract in dose-dependant manner.

TABLE

Influence of Pelargonium extract on the exploration behaviour of mice in a bright-dark box.

| Substance | Dose mg/kg p.o. | Stay in the bright region (seconds) MW ± S.D. | Number of changes of the region |
|---|---|---|---|
| agar + NaCl | | 83 ± 8 | 8.5 ± 2.8 |
| agar + LPS | | 135 ± 34 | 4.4 ± 2.8 |
| Pelargonium extract + LPS | 100 | 119 ± 18 | 5.5 ± 0.8 |
| Pelargonium extract + LPS | 200 | 104 ± 18* | 5.5 ± 1.4 |
| Pelargonium extract + LPS | 400 | 97 ± 11* | 7.5 ± 1.9* |

*$P < 0.05$ (=probability of error), t-test

The invention claimed is:

1. A method for treating a subject suffering from anxiety comprising administering to the subject in need thereof an effective amount of one or more aqueous-ethanolic extracts from plant parts of *Pelargonium* species selected from *Pelargonium sidoides* and *Pelargonium reniforme*.

2. The method of claim 1 wherein the plant parts are roots.

* * * * *